US006454735B1

(12) United States Patent
Hamada

(10) Patent No.: US 6,454,735 B1
(45) Date of Patent: Sep. 24, 2002

(54) SIMPLIFIED BANDAGE USED FOR TORSO

(75) Inventor: Shinichi Hamada, Tokyo (JP)

(73) Assignee: Shunkichi Serizawa, Machida (JP)

( * ) Notice: Subject to any disclaimer, the term of this patent is extended or adjusted under 35 U.S.C. 154(b) by 0 days.

(21) Appl. No.: 09/461,260

(22) Filed: Dec. 15, 1999

(30) Foreign Application Priority Data

Dec. 16, 1998 (JP) ............................................ 10-357382

(51) Int. Cl.⁷ .......................... A61F 13/00; A01K 13/00; A41B 1/12
(52) U.S. Cl. ............................ 602/61; 602/60; 119/850; 2/69
(58) Field of Search .................................. 119/727, 725, 119/792, 856, 907, 850, 868; 602/19, 61; 2/243, 48, 246, 49.1, 49.2, 49.3, 49.4, 49.5

(56) References Cited

U.S. PATENT DOCUMENTS

| 2,845,064 | A | * | 7/1958 | Walsh | |
| 4,137,870 | A | * | 2/1979 | Cano | |
| 4,489,676 | A | * | 12/1984 | Colquist | |
| 4,577,591 | A | * | 3/1986 | Wesseldine | |
| 5,632,235 | A | * | 5/1997 | Larsen et al. | 119/856 |
| 5,896,831 | A | * | 4/1999 | Alpert | 119/856 |
| 5,984,855 | A | * | 11/1999 | DiNapoli | 600/15 |
| 6,009,839 | A | * | 1/2000 | Kohn | 119/770 |
| 6,119,635 | A | * | 9/2000 | Powell-Lesnick | 119/850 |
| 6,123,049 | A | * | 9/2000 | Slater | 119/850 |
| 6,223,696 | B1 | * | 5/2001 | Murakami | 119/850 |

* cited by examiner

Primary Examiner—Kim M. Lewis
(74) Attorney, Agent, or Firm—Oppenheimer Wolff & Donnelly, LLP

(57) ABSTRACT

A bandage for a torso of a patient comprises a sheet part having a sheet member piece which for covering of a patient's torso, a neck fastening member for fastening the upper edge of the sheet part to a neck of the patient, an underarm fastening member to fasten the middle part of the sheet part to a body trunk part of the patient, and a waist fastening member to fasten the lower edge of the sheet part to a waist of the patient. The sheet part includes a abdomen covering part in a two substantially -equal-sided trapezoidal shape. The base is shorter than the top. The upper abdomen covering part is a rectangular shape in which the top of the lower abdomen covering part is the bottom side. The chest covering part is a two-substantially equal-sided trapezoid shape in which the top side of the upper abdomen covering part is the base and the top is shorter than the base. The neck covering part is a substantially rectangular shape in which the top of the chest covering part is the bottom side. The sheet part, when not in use, is gathered in the connecting direction of the respective parts by elastic members on at least one of the two outer sides of the covering part, the lower abdomen covering part, upper abdomen covering part, and chest covering part. It is stretchable in the connecting direction as necessary when in use.

10 Claims, 2 Drawing Sheets

SIMPLIFIED BANDAGE USED FOR TORSO

BACKGROUND OF THE INVENTION

The present invention concerns a bandage used to cover and protect an affected area of a person or animal. Specifically, it concerns a simplified bandage used for the torso which is suitable for protecting an affected area in the chest area or the abdomen.

In the treatment of an external injury of a person or animal such as a cat or dog, a bandage is used and this is constituted by a piece of cloth of narrow width and long length which is used as a bandage to cover an affected injury area.

For example, in cases where a relatively thin affected area such as a leg or arm of a person or animal such as a cat or dog is covered, the action required to wrap the bandage is minimum, and it does not cause much of an inconvenient feeling.

However, in cases where the affected area is in the chest or abdomen, the part to wrap the bandage is wrapped around relatively thick part of the chest or waist. Accordingly, it is not easy to wrap many times a bandage of short width and long length. In particular, in cases where the conventional bandage is wrapped to cover the stitched part after a laparotomy, the body of a patient laid down on a bed needs to be lifted from the bed several times in order to wrap the bandage around the body trunk of a patient who has just undergone the operation. This is hard work for both the patient who underwent the operation and the caretaker.

The present invention provides a bandage which meets needs for a comfortable bandage that allows the protection of the affected area such as the chest part or abdomen, and the fixation of the surgical dressing applied to the affected area. An object of the present invention is to provide a simplified bandage used for the torso for a person or animal such as a cat or dog.

Additionally, the bandage provides a hygenic protection which provides protection and also some ventilation. This helps keep the affected area dry. This is believed important to assist the affected part to recover smoothly.

SUMMARY OF THE INVENTION

In order to achieve the above object, a simplified bandage is used for the torso.

The bandage comprises a sheet part constituting a piece of sheet member which allows the covering of the torso of a patient, a neck fastening member to fasten the upper edge of the sheet part to the neck of the patient, an underarm fastening member to fasten the middle part of the sheet part to the body trunk part of the patient, and a waist fastening member to fasten the lower edge of the sheet part to the waist of the patient.

The sheet part constitutes the lower abdomen covering part in a two-equal-sided trapezoidal shape in which the base is shorter than the top, the upper abdomen covering part in a rectangular shape in which the top of the lower abdomen covering part is the bottom side, the chest covering part is a two-equal-sided trapezoidal shape in which the top side of the upper abdomen covering part is the base and the top is shorter than the base, and the neck covering part is a rectangular shape in which the top of the chest covering part is the bottom side.

The sheet part is constituted so that when it is not in use it is gathered in the connecting direction of the respective parts by means of elastic members provided on at least one of both outer sides of the covering part among the lower abdomen covering part, upper abdomen covering part, and chest part covering part. It can stretch in the connecting direction as necessary when it is used.

The present invention makes it possible to cover the patient's chest, upper abdomen, and lower abdomen easily and properly by applying the sheet part which is gathered by means of the elastic members to the patient's affected area, and by fastening the sheet part to the patient's body using the neck fastening member, underarm fastening member, and waist fastening member.

Moreover, the simplified bandage used for the torso is a simplified bandage used for the torso. The elastic members are preferably a string-shaped elastic band member.

The present invention allows the sheet part to fit the patient's body easily.

The sheet member is formed of a non-woven material. The present invention provides a bandage which can be easily processed for antibacterial processing for a non-woven material, and does not require processing of the cutoff part.

Accordingly, the present invention significantly contributes to improvement in hygiene and cost, providing improved comfort in use.

The simplified bandage used for the torso includes a sheet part which allows the formation of a cut-out part for urination. It is possible to form the cut-out part for urination for a male human or animal easily by cutting out a part of the sheet member as necessary.

DETAILED DESCRIPTION OF THE PREFERRED EMBODIMENT

Figure 1:
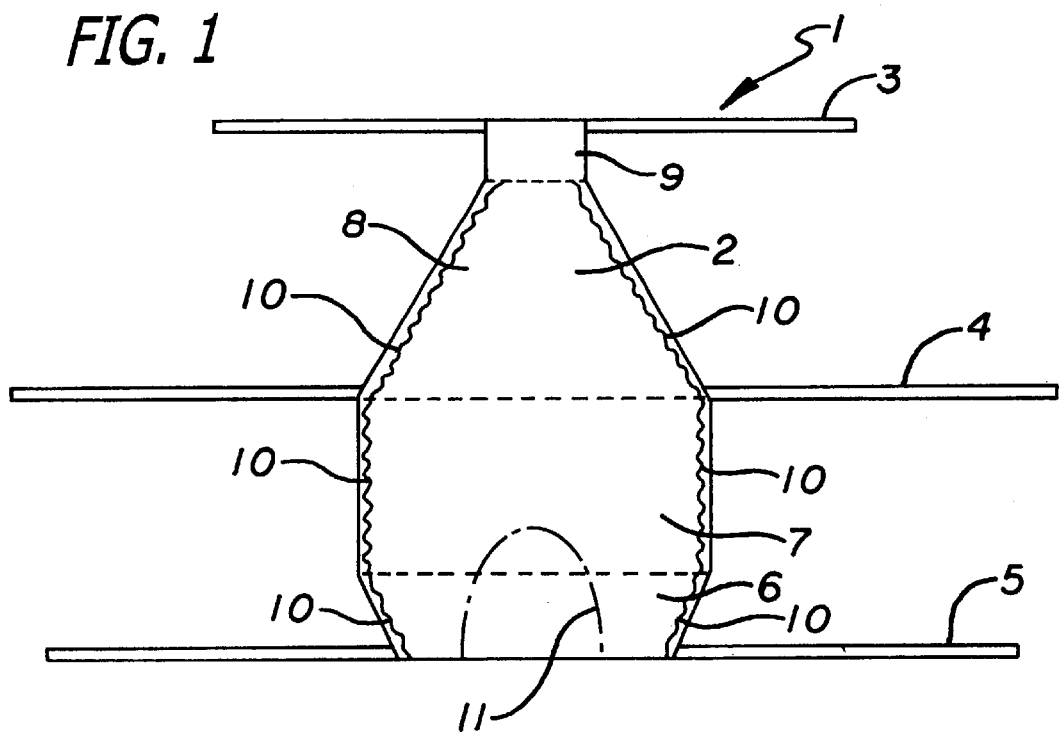
FIG. 1 shows the plane that indicates a working configuration of the simplified bandage used for the torso of the present invention.

EXPLANATION OF SYMBOLS 1 simplified bandage used for the torso
2 sheet part
3 neck fastening member
4 underarm fastening member
5 waist fastening member
6 lower abdomen covering part
7 upper abdomen covering part
8 chest covering part
9 neck covering part
10 elastic members (round elastic strings)
11 cut-out part A working configuration is described with reference to FIGS. 1 through 3.

A simplified bandage used for the torso 1 of the present working configuration, is shown in FIG. 1. It constitutes a sheet part 2 consisting of a sheet member piece, a neck fastening member 3 which is used to fasten the upper edge of the aforementioned sheet part 2 to the neck of the patient who wears the bandage, an underarm fastening member 4 used to fasten the middle part of the aforementioned sheet part 2 to the patient's chest, and a waist part fastening member 5 used to fasten the lower edge of the aforementioned sheet part 2 to the patient's waist.

The sheet part 2 constitutes the lower abdomen covering part 6 which is formed in a two-equal-sided trapezoidal shape. The base is shorter than the top and functions to cover and protect the lower abdomen of the patient when in use, the upper abdomen covering part 7 which is formed in a rectangular shape. The top of the lower abdomen covering part 6 composes the bottom side and functions to cover and protect the patient's upper abdomen, the chest covering part 8 in a two-equal-sided trapezoid. The top side of the upper abdomen covering part 7 composes the base and the top is shorter than the base and functions to cover and protect the patient's chest when in use. The rectangular neck covering part 9 in which the top of the chest covering part 8 makes the bottom side and functions to cover and protect the patient's neck when in use. Furthermore, in FIG. 1, the division of the neck covering part 9, chest covering part 8, upper abdomen covering part 7, and lower abdomen covering part 6 is indicated by the dotted line.

Round elastic strings 10 as elastic members are sewn onto the outer side part of the lower abdomen covering part 6, upper abdomen covering part 7, and chest covering part 8 of the sheet part 2. These round elastic strings 10 are sewn onto the sheet member of the sheet part 2 in the stretched state. FIG. 1 shows this state. When it is not in use, gathers are formed as a result of the contraction of the round elastic strings 10, and the contraction of the lower abdomen covering part 6, upper abdomen covering part 7, and chest covering part 8 in the connecting direction. When it is used, the bandage is constructed so that the bandage fits on the patient by stretching appropriately in the connecting direction according to the patient's body. Furthermore, in the present working configuration, the sheet member constituting the sheet part 2 is made from a non-woven material, and the non-woven material is processed with an anti-bacterial treatment.

The neck fastening member 3 in the present working configuration is a pair of flat string members made from the same non-woven material as the sheet member. One edge is attached to both sides of the top side of the neck covering part 9, respectively.

In the same manner, the underarm fastening member 4 and waist part fastening member 5 are a pair of flat string members which are made from the same non-woven material as the sheet member. The underarm fastening member 4 has one end of the flat string member fastened to both sides of the boundary part of the chest covering part 8 and upper abdomen covering part 7 of the sheet part 2, respectively. The waist fastening part 5 has one end of the flat string member fastened to both sides of the bottom side of the lower abdomen covering part 6 of the sheet part 2.

Next, the method of use of the simplified bandage used for the torso 1 of the present working configuration is described.

The simplified bandage used for the torso 1 of the present working configuration is provided with several different sizes with different widths as well as the length of the sheet part 2. Then, the simplified bandage used for the torso 1 that is bigger than the torso of a person or animal as a user of the simplified bandage used for the torso (hereafter referred to as patient), is selected and put on the patient.

First, the sheet part 2 is positioned on the front side of the patient's body so that the affected area that has been treated and covered with a surgical dressing or bandage can be further widely covered. The open edge sides of the neck fastening member 3, which is fastened to both sides of the top edge of the sheet part 2, are tied on the back side around the neck part from the left and right of the patient's body, respectively. The neck covering part 9 of the sheet part 2 is fastened to the patient's neck. In this state, the upper edge of the simplified bandage used for the torso 1 of the present working configuration will be fastened to the patient's neck.

At this time, in cases where there is no need to protect the neck, the length of the patient's neck is short, or no appropriate size is available among the sizes of the simplified bandage used for the torso 1 that are prepared in advance.

Figure 2:
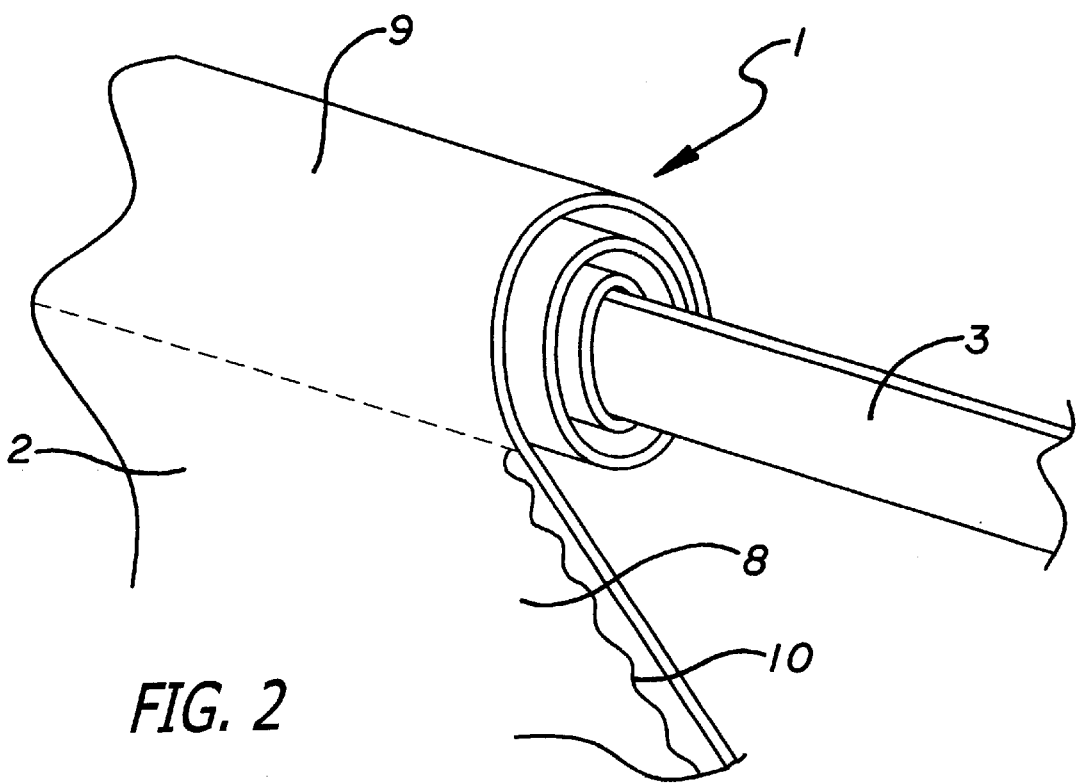
FIG. 2 shows the explanatory diagram of important parts which indicates the state when the simplified bandage used for the torso in FIG. 1 is in use.

The simplified bandage used for the torso 1 to be used is slightly bigger than the patient's body, as is shown in FIG. 2. The neck covering part 9 or the sheet part 2 is adjusted by rolling up the neck covering part 9 which is formed in a rectangular shape with a certain width from the upper edge side so that the length is appropriate for the patient's body size. The neck fastening member 3 extends from both edges of the rolled-up part of the neck covering part 9 is put around the patient's neck to be tied.

Next, the chest covering part 8, in which several gathers are formed, is contracted in the direction of the length of the sheet part 2. As a result of the contraction of the round elastic strings 10 used as elastic members sewn onto both sides is adjusted to an appropriate length while stretching the round elastic string 10 according to the patient's body. The open edge sides of the underarm fastening member 4 are put around the body trunk under the underarm from the left and right of the patient's body to be tied on the back side. The chest covering part 8 of the sheet part 2 is fixed to the patient's chest. In this state, the simplified bandage used for the torso 1 of the present working configuration can cover and protect the patient's chest.

At this time, the chest covering part 8 of the simplified bandage used for the torso 1 before being put on the patient, fits the patient's chest in the stretched state in the direction of the length appropriately according to the patient's body size by stretching the round elastic strings 10 which is provided between the neck fastening member 3 and underarm fastening member 4.

Furthermore, in the present working configuration, the simplified bandage used for the torso securely covers the chest in the state in which the shoulders are exposed when in use as a result of making the shape of the aforementioned chest covering part 8 a two-equal-sided trapezoid in which the top is smaller than the base.

Next, the upper abdomen covering part 7 and the lower abdomen covering part 6 in which several gathers are formed is contracted in the direction of the length of the sheet part 2. As a result of the contraction of the round elastic strings 10, as elastic members sewn onto both sides, are. adjusted to an appropriate length by stretching the round elastic strings 10 according to the patient's body. The open edge sides of the waist fastening member 5 fastened to both sides of the bottom part of the sheet 2 are put around the waist from the left and right of the patient's body to be tied on the back side. The upper abdomen covering part 7 and lower abdomen covering part 6 of the sheet part 2 are fastened to the patient's abdomen. In this state, the simplified bandage used for the torso 1 of the present working configuration can cover and protect the patient's abdomen.

At this time, the upper abdomen covering part 7 and lower abdomen covering part 6 fit the patient's abdomen in the stretched state in the direction of the length appropriately according to the patient's body by stretching the round elastic strings 10 provided between the underarm fastening member 4 and waist fastening member 5 by fastening the bottom edge position of the lower abdomen covering part 6 to the underarm fastening member 4.

Furthermore, there are cases where the lower abdomen does not need to be protected, or the simplified bandage used for the torso 1 to be used is bigger than the patient's body. The neck fastening member 3 is used. It is possible to adjust the lower abdomen.covering part 6 which is formed in a two-equal-sided trapezoid with the base being shorter than the top by rolling it up at a certain width from the bottom edge side so that the length of the lower abdomen covering part 6 or the sheet part 2 fits the patient's body size, and the waist fastening member 5 extending from both edges of the rolled-up lower abdomen covering part 6 are put around the patient's waist to be tied on the back side.

Figure 3:
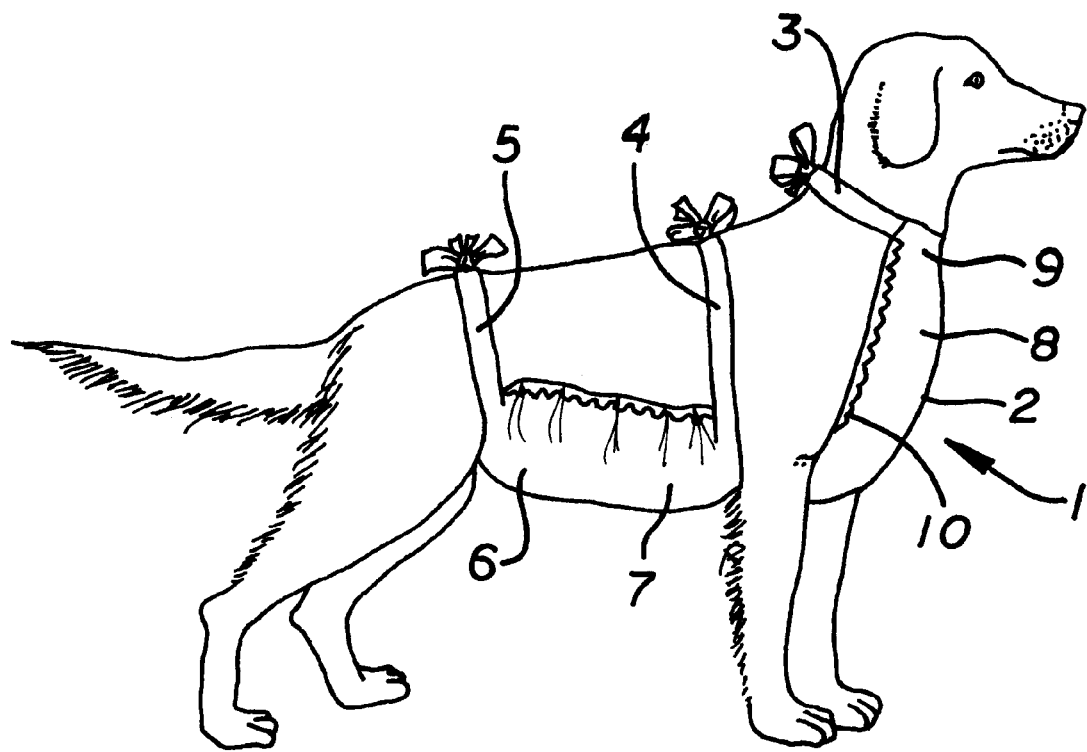
FIG. 3 shows the explanatory diagram which indicates a case where the simplified bandage used for the torso of the present working configuration is used for a dog.

FIG. 3 shows a case in which the simplified bandage for the torso of the present working configuration is put on a dog as a patient in the manner described earlier.

Moreover, for example, in cases when the simplified bandage used for the torso is used for a patient who underwent laparotomy, the sheet part 2 can be put on the patient's body by laying the simplified bandage used for the torso 1. This is adjusted to the size of the patient's body in advance, on the bed in an open state, laying the patient with his/her face sideways in the direction in which the bandage 1 extends widely on one side of the sheet member of the simplified bandage used for the torso 1, and tying the neck fastening part 3, underarm fastening member 4, and waist fastening member 5 in that position.

In this way, the simplified bandage used for the torso 1 allows the affected area of the torso to he covered easily and securely, thus minimizing the labor for both patient and caretaker. Moreover, the simplified bandage used for the torso 1 put on in this manner forms the gathers by means of the elastic members on both sides of the chest covering part 8, upper abdomen covering part 7, and lower abdomen covering part 6. These gathers are stretched appropriately according to the patient's body; accordingly, the simplified bandage used for the torso 1 fits the patient's body tightly, and the affected area is isolated from the outside and can be securely covered, thus allowing the protection of the affected area and the fixation of the surgical dressing for the treatment that is applied to the affected area.

Furthermore, the simplified bandage used for the torso 1 of the present working configuration, for example in cases where it is used for a man or male animal, allows the formation of a cut-out part for urination 11 by cutting out the center of the bottom edge side of the sheet part 2 in a u-shape as necessary, as shown by the dotted line in FIG. 1. Moreover, by producing the simplified bandage used for the torso 1 of the present working configuration using a non-woven material, the formation of the cut-out part 11 can be performed easily, without any unraveling. Furthermore, the cut-out part for urination 11 may be formed in a manner so that the cutout part can he cut out using the perforated line formed with dotted lines provided beforehand.

Moreover, since the simplified bandage used for the torso 1 can be easily made for a man or male animal by cutting out the basic shape of the simplified bandage used for the torso 1, there is no need for the simplified bandage used for the torso 1 to be manufactured taking into account sex, whether for man/male or woman/female. Thus, the mass production of the basic shape of the simplified bandage used for the torso 1 with different sizes would be sufficient, and if the mass production performed in this manner is possible, it will be possible to lower the cost as well.

Furthermore, the simplified bandage used for the torso 1 of the present working configuration allows the covering of the affected area widely and completely. Thus, it is possible to prevent the affected area or the medicine applied to the affected area from being licked even when the bandage is used for an animal such as a cat or dog that has a habit of licking the affected area; thus, the affected area can be maintained hygienically.

Moreover, if the cost is reduced, the simplified bandage used for the torso 1 used can become disposable and sanitary. As described above, the bandage can be much more sanitary if anti-bacterial processing is performed for the non-woven material constituting the sheet member. Furthermore, the non-woven material can be burned; the process is also simple.

The present invention is not limited to the aforementioned working configuration, but can be varied as necessary.

For example, the neck fastening member, underarm fastening member, and waist fastening member can be provided with a flat-surface zipper, what's called Velcro™, and fastened by means of the Velcro™, instead of a type being tied on the back side of the body, or a fastening member comprising, for example, one string member and D-ring, instead of the two flat strings as described earlier, can be used.

Furthermore, the elastic members which are provided in the aforementioned chest covering part, upper abdomen covering part, and lower abdomen covering part are voluntary; any or all of the elastic members may be omitted.

As described above, the simplified bandage used for the torso of the present invention can be put on so that the following effects can be achieved; the affected area in the torso of a person or animal such as a cat or dog may be easily and securely covered, it is good in terms of hygiene, it can be mass-produced, the cost can be lowered, and comfort can be improved.

It is easy and quick to put the dressing on the patient body or torso. The dressing also serves to keep the affected area less wet and tight. This accommodates some ventilation through the protection dressing which is important to help the affected area to remain dry. This leads to faster and quicker recovery.

Moreover, there can be a combination of a cotton liner or pad with this dressing to help achieve this objective. This pad can be located in a strategic location relative to the bandage, for instance underneath the bandage in a position adjacent to a wound. In other cases, it can be removed from direct contact with the wound.

What is claimed is:

1. A bandage for a torso of a patient comprising
   a sheet part having a sheet member piece for covering of a patient's torso;
   a neck fastening member for fastening the upper edge of the sheet part to a neck of the patient,
   an underarm fastening member to fasten the middle part of the sheet part to a body trunk part of the patient;
   a waist fastening member to fasten the lower edge of the sheet part to a waist of the patient;
   the sheet part including
   an abdomen covering part, and
   a chest covering part,
   a neck covering part being on top of the chest covering part; and
   the sheet part, when not in use, being gathered by elastic members on at least one of the two outer sides of the covering part among the lower abdomen covering part, upper abdomen covering part, and chest covering part, and being stretchable in the connecting direction as necessary when in use.

2. A bandage as defined in claim 1 wherein the elastic members are string-form elastic members.

3. A bandage as defined in claim 1 or claim 2, wherein the sheet member piece includes a non-woven material.

4. A bandage as defined in claim 3 wherein the sheet part includes a cut-out part for urination.

5. A bandage as defined in claim 1 or claim 2 wherein the sheet part includes a cut-out part for urination.

6. A bandage for a torso of a patient comprising:

a sheet part having a sheet member piece for covering of a patient's torso;

a neck fastening member for fastening the upper edge of the sheet part to a neck of the patient, an underarm fastening member to fasten the middle part of the sheet part to a body trunk part of the patient;

a waist fastening member to fasten the lower edge of the sheet part to a waist of the patient;

the sheet part including an abdomen covering part including two substantially equal-sided trapezoidal shapes, in which a base is shorter than a top, there being an upper abdomen covering part being a rectangular shape, and a lower abdomen covering part, and a chest covering part being two-substantially equal-sided trapezoid shapes in which the top of the upper abdomen cover part is the base and the top is shorter than the base, a neck covering part being a substantially rectangular shape in which the top of the chest covering part is the bottom side; and the sheet part, when not in use, being gathered by elastic members on at least one of the two outer sides of the covering part among the lower abdomen covering part, upper abdomen covering part, and chest covering part, and being stretchable in the connecting direction as necessary when in use.

7. A bandage as defined in claim 6 wherein the elastic members are string-form elastic members.

8. A bandage as defined in claim 6 or claim 7, wherein the sheet member piece includes a non-woven material.

9. A bandage as defined in claim 6 or claim 7 wherein the sheet part includes a cut-out part for urination.

10. A bandage as defined in claim 8 wherein the sheet part includes a cut-out part for urination.

* * * * *